US005552549A

United States Patent [19]

Rasp et al.

[11] Patent Number: 5,552,549

[45] Date of Patent: Sep. 3, 1996

[54] PROCESS FOR THE DECHLORINATION OF CHLORINATED AROMATIC COMPOUNDS

[75] Inventors: Christian Rasp, Bergisch Gladbach; Helmut Waldmann; Hans-Joachim Traenckner, both of Leverkusen, all of Germany

[73] Assignee: Bayer Aktiengesellschaft, Leverkusen, Germany

[21] Appl. No.: 315,001

[22] Filed: Sep. 29, 1994

[30] Foreign Application Priority Data

Oct. 6, 1993 [DE] Germany .......................... 43 34 056.3

[51] Int. Cl.[6] ...................... C07D 217/00; C07D 309/00; C07C 22/00; C07C 1/20

[52] U.S. Cl. .......................... 546/139; 546/180; 546/181; 546/345; 546/348; 549/357; 549/369; 549/380; 568/635; 568/639; 570/204; 585/469

[58] Field of Search .................................... 570/190, 204, 570/205; 546/139, 180, 181, 345, 348; 568/630, 663, 639, 635; 585/469; 549/357, 369, 380

[56] References Cited

U.S. PATENT DOCUMENTS

| | | | |
|---|---|---|---|
| 4,188,346 | 2/1980 | Markley | 570/24 |
| 4,337,368 | 6/1982 | Pytlewski et al. | 570/204 |
| 4,422,872 | 12/1983 | Geskin | 75/51 |
| 4,574,714 | 3/1986 | Bach | 110/346 |
| 4,601,817 | 7/1986 | Globus | 208/262 |
| 4,602,574 | 7/1986 | Bach et al. | 110/346 |
| 4,816,609 | 3/1989 | Harley | 570/204 |
| 5,108,647 | 4/1992 | Bolsing | 570/204 |
| 5,243,110 | 9/1993 | Sola et al. | 570/204 |
| 5,369,214 | 11/1994 | Farcasiu et al. | 570/204 |

FOREIGN PATENT DOCUMENTS

WO9310862 6/1993 WIPO .

WO9320898 10/1993 WIPO .

OTHER PUBLICATIONS

Helv. Chim. Acta, vol. 51, pp. 2090–2097, 1968; R. A. Egli et al, Abstract #0467, "Kataly. Dehalogenierunger mit Natriumborhydrid".

Tetrahedron Letters, 1969, vol. 16, pp. 1223–1226; P. Olavi, Abstract #0414, "Hydrogenolyse der Chlorbenzole mit Lithiumaluminium hydrid".

STN International, Jul. 29, 1993, p. 7; Environ. Sci. Technol., vol. 21, pp. 1085–1088; "Copper-catalyzed dechlorination/hydrogenation of . . . ", H. Hagenmaier.

25–Benzenes, vol. 117, 1992; J. Chem. Soc. Chem. Commun., 1992, pp. 806–807, vol. 11; CA#89927n, "Hydrodechlorination of chloroaromatics", D. T. Ferrughelli et al.

JPA 12694/65, Mitto Chem. Ind. Co., Jun. 21, 1965; "Die selektive dechlorierung von Polychlortolueolen"; p. 28.

JPA 24776/65, Mitusi Chem. Ind. Co., Oct. 29, 1965; "Polychlortoluole", p. 24.

STN International, Jul. 29, 1993, p. 8; USA 4601817, Jul. 22, 1986; "Treatment of hazardous material", A. R. Globus.

72–Electrochemistry, vol. 113, 1990; Z. Naturforsch, B: Chem. Sci., 1990, vol. 45, pp. 1105–1107; CA# 161076w, "Electroreduction of organic compounds . . . ", D. Petersen.

Tetrahedron Letters, 1979, vol. 22, pp. 2059–2062; G. G. Choudhyr et al, Abstract # 7837–180, "Photochemistry of halogenated benzene derivatives . . . ".

Chem. Letters, vol. 10, pp. 2051–2052; "Transchlorination of o–dichlorobenzene and benzene into chlorobenzene", K. Shinoda; 1987.

*Primary Examiner*—Alan Siegel

*Attorney, Agent, or Firm*—Sprung Horn Kramer & Woods

[57] ABSTRACT

Chlorinated aromatic compounds are dechlorinated in a simple and inexpensive manner by heating them to 300° to 450° C. in a salt melt in the presence of water and/or water vapor and carbon.

8 Claims, No Drawings

PROCESS FOR THE DECHLORINATION OF CHLORINATED AROMATIC COMPOUNDS

The present invention relates to a process for the dechlorination of chlorinated aromatic compounds to form lower-chlorine and/or chlorine-free aromatic compounds.

Relatively highly chlorinated aromatic compounds, such as are obtained, for example, as by-products in the preparation of aromatic compounds having a low degree of chlorination, as spent functional liquids (for example transformer oils) or as by-products in the combustion of the most diverse chlorinated organic compounds, are often environmental pollutants. They can be converted into reusable materials or burned by-known processes only in an expensive manner.

Processes are thus known in which the dechlorination is carried out with hydrogen or other reducing agents in the presence of catalysts (see Helv. Chim. Acta 51, 8290–8297 (1968); Tetrahedron Letters 1969, 1223–1226; Environ. Sci. Technol. 21, 1085–1088; J. Chem. Soc. Chem. Comm. 1992, 806–807; JP-A 12 694/65; and JP-A 24 776/65), in which reactions with elemental sodium are necessary (see, for example, U.S. Pat. No. 4,601,817), in which electrochemical reduction is carried out (Z. Naturforsch., B: Chem. Sci. 45, 1105–1107 (1990)) and in which photolysis is carried out (see Tetrahedron Letters 22, 2059–2062 (1979)). The keeping ready and handling of hydrogen and other reducing agents, catalysts, elemental sodium and special equipment are disadvantages here.

Transchlorination processes furthermore are known, in which chloroaromatics having average degrees of chlorination are obtained from aromatics having a higher degree of chlorination and aromatics having a lower degree of chlorination or chlorine-free aromatics in a type of comproportionation reaction (see, for example, Chem. Lett. 1987, 2051–2052). The use of additional aromatics (of lower degree of chlorination or chlorine-free) to remove chlorine from aromatics having a higher degree of chlorination is a disadvantage.

During the known combustion processes on chlorinated aromatics, either usable, low-boiling compounds and undefined compositions, for example chlorine-containing tars, or, at higher temperatures, practically only hydrogen chloride and carbon black are formed. Chlorine-containing tars are likewise environmental pollutants, and the aromatic parent substance is lost in the formation of carbon black.

There is therefore still a need for a simple and inexpensive process for the dechlorination of chlorinated aromatic compounds, in which their chlorine content is lowered or eliminated completely and the aromatic parent substance is retained for further chemical uses.

A process has now been found for the dechlorination of chlorinated aromatic compounds, which is characterized in that chlorinated aromatic compounds are heated at 300° to 450° C. in a salt melt in the presence of water and/or water vapour and carbon.

Possible chlorinated aromatic compounds for use in the process according to the invention are, for example, those which are derived from benzene, pyridine, naphthalene, quinoline, isoquinoline, diphenyl ether or dioxin as the parent substance. They contain, per molecule, at least one chlorine atom bonded to the parent substance. Preferably, they contain from two to the maximum possible number of chlorine atoms, that is to say, for example, 2 to 6 chlorine atoms in the case of a benzene parent substance, 2 to 5 chlorine atoms in the case of a pyridine parent substance, 2 to 8 chlorine atoms in the case of a naphthalene parent substance, 2 to 7 chlorine atoms in the case of a quinoline or isoquinoline parent substance, 2 to 10 chlorine atoms in the case of a diphenyl ether parent substance and 2 to 8 chlorine atoms in the case of a dioxin parent substance.

Chlorinated aromatic compounds which can be employed in the process according to the invention can optionally contain other substituents, in addition to chlorine atoms. Such other substituents can be, for example, $C_1$–$C_4$-alkyl, $C_6$–$C_{10}$-aryl, $C_1$–$C_4$-alkyl-$C_6$–$C_{10}$-aryl, mono- to trichloro-$C_1$–$C_4$-alkyl or mono- to pentachloro-$C_6$–$C_{10}$-aryl.

Compounds which are preferably employed in the process according to the invention are: chlorobenzene, 1,2-, 1,3or 1,4-dichlorobenzene, 1,2,3-, 1,2,4- or 1,3,5-trichlorobenzene, tetra-, penta- or hexachlorobenzene, mono- or polychlorotoluenes, mono- or polychloroxylenes or chlorinated biphenyls.

It is of course also possible to employ any desired mixtures of various chlorinated aromatic compounds in the process according to the invention.

Possible salts for the formation of the salt melt are, for example, inorganic, ionic salts and mixtures comprising these, if they have a melting point below 450° C. The melting point of the salt or salt mixture employed is preferably below 360° C., particularly preferably below 300° C.

The salt melt can comprise, for example, chlorides, such as lithium chloride, sodium chloride, potassium chloride, zinc chloride, copper(I) chloride, copper(II) chloride, silver chloride, thallium chloride, tin(II) chloride, aluminium chloride and/or iron(III) chloride. Mixtures which comprise zinc chloride, copper(I) chloride, copper(II) chloride and/or potassium chloride are preferred. Mixtures of copper(I) chloride and potassium chloride are particularly preferred, especially those which comprise 50 to 90% by weight of copper(I) chloride and potassium chloride to make up to 100% by weight.

1 to 20 kg of the particular salt melt can be employed, for example, per 100 g of chlorinated aromatic compounds employed in the process according to the invention.

Preferred temperatures for carrying out the process according to the invention are those in the range from 350° to 400° C. particularly preferably those in the range from 360° to 385° C.

The pressure in the process according to the invention can be varied within wide limits. In the simplest case, the process according to the invention is carried out in a closed vessel under the pressure established by itself or under the pressure determined by a pressure retention valve. Suitable pressures are, for example, in the range from 1 to 50 bar. Preferred pressures are in the range from 5 to 20 bar.

Water and carbon, the latter preferably in pulverulent form, can be added to the process according to the invention as such or in the form of a so-called carbon slurry, that is to say in the form of a pumpable mixture which contains ground carbon and water. The carbon and/or the water can also be formed in situ under the reaction conditions, for example from added substances which tend to carbonize and/or split off water at elevated temperature. Such substances are, for example, sugars, such as sucrose, molasses and modified sugars, such as propoxylated sucrose. Such substances can also be employed in the form of an aqueous solution. Ground, sulphur-free carbon and, for example, active charcoal accessible from sugar or molasses are preferably employed.

In general at least ½ mol of water and ¼ g atom of carbon are added per g atom of chlorine to be split off from the chlorinated aromatic compounds, but larger excesses are also possible, for example up to 1 mol of water and up to 0.5 g atom of carbon per g atom of chlorine to be split off from the chlorinated aromatic compounds.

The process according to the invention can be carried out discontinuously or continuously. In the continuous procedure, for example, 0.1 to 1 mol of chlorinated aromatic compounds can be reacted with 0.5 l of salt melt per hour in a reactor of 1 l capacity. It is advantageous to stir the mixture when carrying out the process according to the invention.

Since both the salt melt and the hydrogen chloride formed are corrosive, it is advantageous to use reaction vessels which have been given an anticorrosive treatment, for example by lining with tantalum. The dechlorination reaction stops in the absence of water or water vapour or carbon.

The process according to the invention gives aromatic compounds which contain less chlorine than the starting compound(s) and/or no longer contain chlorine. In addition, hydrogen chloride, carbon dioxide and carbon monoxide are formed. Undefined by-products, such as tar or carbon black, are hardly formed at all from the chlorinated aromtic compounds employed.

The gaseous reaction products can be separated off from the reaction mixture by letting down or via a pressure retention valve. The resulting low chlorine and chlorine-free aromatic compounds can be separated off and isolated by fractional distillation and used further in several ways, for example as intermediate products for the preparation of active compounds. Unreacted starting compounds and reaction products which are still relatively highly chlorinated can be fed again to the process according to the invention, if appropriate. The salt melt can be reused, if appropriate after renewed metering in of water and/or carbon.

The process according to the invention allows aromatic compounds having a relatively high degree of chlorination to be converted into reusable aromatic compounds which have a low degree of chlorination or are chlorine-free in a simple and inexpensive manner.

EXAMPLES

Example 1

720 g of copper(I) chloride, 280 g of potassium chloride, 6 g of sucrose and 18.15 g of 1,2,4-trichlorobenzene were initially introduced into a pressure reactor of 1 l capacity lined with tantalum. The pressure reactor was then closed and heated to 375° C. while stirring vigorously. After 1 hour, the reactor was cooled and let down, and the organic constituents of the reaction mixture were analyzed quantitatively. More than 95% by weight of the 1,2,4-trichlorobenzene employed had been converted into a mixture which comprised 8% by weight of 1,2-dichlorobenzene, 35% by weight of 1,3-dichlorobenzene, 44.6% by weight of 1,4-dichlorobenzene, 10.8% by weight of monochlorobenzene and 1.4% by weight of benzene.

Example 2

The procedure was as in Example 1 but, instead of sucrose, 1 g of water and 6 g of active charcoal were employed. After 1 hour, more than 95% by weight of the 1,2,4-trichlorobenzene employed had been converted into a mixture which comprised 6.8% by weight of 1,2-dichlorobenzene, 35.7% by weight of 1,3-dichlorobenzene, 44.1% by weight of 1,4-dichlorobenzene, 11.7% by weight of monochlorobenzene and 1.3% by weight of benzene.

Example 3 (for Comparison)

The procedure was as in Example 1 but, instead of sucrose, 3 g of active charcoal were employed. After 1 hour, only 2% by weight of the 1,2,4-trichlorobenzene employed had been converted.

This example shows that the presence of water or water vapour is essential to the invention.

Example 4 (for Comparison)

The procedure was as in Example 1 but, instead of sucrose, 1 g of water was added. After 1 hour, only 1.5% by weight of the 1,2,4-trichlorobenzene employed had been converted.

This example shows that the presence of carbon is essential to the invention.

What is claimed is:

1. A process for the at least partial dechlorination of at least one chlorinated aromatic compound selected from the group consisting of benzene, pyridine, naphthalene, quinoline, isoquinoline, and diphenyl ether or dioxin, which compound contains at least two chlorine atoms, which comprises heating said compound to 300° to 450° C. in a melt comprising at least one salt selected from the group consisting of lithium chloride, sodium chloride, potassium chloride, zinc chloride, copper(I) chloride, copper(II) chloride, silver chloride, thallium chloride, tin(II) chloride, aluminum chloride and iron(III) chloride, in the presence of water and carbon.

2. The process of claim 1, in which water vapour is present.

3. The process of claim 1, in which the chlorinated compound contains one or more substituents from the group consisting of $C_1$–$C_4$-alkyl, $C_6$–$C_{10}$-aryl, $C_1$–$C_4$-alkyl-$C_6$–$C_{10}$-aryl, mono- to trichloro-$C_1$–$C_4$-alkyl or mono- to pentachloro-$C_6$–$C_{10}$-aryl in addition to chlorine atoms.

4. The process of claim 1, which is carried out at temperatures in the range from 350° to 400° C.

5. The process of claim 1, which is carried out under pressures in the range from 1 to 50 bar.

6. The process of claim 1, in which ground, sulphur-free carbon or active charcoal accessible from sugar or molasses is employed as the carbon.

7. The process of claim 1, in which water and carbon are formed in situ from sugar or molasses.

8. The process of claim 1, in which at least ½ mol of water and at least ¼ g atom of carbon are employed, or can be formed in situ, per g atom of chlorine to be split off from the chlorinated aromatic compounds.

* * * * *